United States Patent [19]
King et al.

[11] Patent Number: 5,351,127
[45] Date of Patent: Sep. 27, 1994

[54] SURFACE PLASMON RESONANCE MEASURING INSTRUMENTS

[75] Inventors: David A. King, Palo Alto, Calif.; Jens-Peter Seher, Stuttgart, Fed. Rep. of Germany

[73] Assignee: Hewlett-Packard Company, Palo Alto, Calif.

[21] Appl. No.: 900,217

[22] Filed: Jun. 17, 1992

[51] Int. Cl.$^5$ .................. G01N 21/55; G01N 21/63
[52] U.S. Cl. .................. 356/445; 356/136
[58] Field of Search .................. 356/445, 136

[56] References Cited

U.S. PATENT DOCUMENTS

| | | | |
|---|---|---|---|
| 4,087,159 | 5/1978 | Ulrich | 385/39 |
| 4,432,614 | 2/1984 | McNeill et al. | 359/261 |
| 4,844,613 | 7/1989 | Batchelder et al. | 356/445 |
| 4,889,427 | 12/1989 | Van Veen et al. | 356/445 |
| 5,023,053 | 6/1991 | Finlan | 356/445 |
| 5,075,796 | 12/1991 | Schildkraut et al. | 385/8 |

FOREIGN PATENT DOCUMENTS 2578978  9/1986  France .................. 356/136

OTHER PUBLICATIONS

Otto, Andreas. "Excitation of Nonradiative Surface Plasma Waves in Silver by the Method of Frustrated Total Reflection" *Zeitschrift fur Physik*, 216, 398–410 (1968).

*Primary Examiner*—Richard A. Rosenberger

[57] ABSTRACT

A measuring instrument utilizing surface plasmon resonance is described. The instrument employs no moving mechanical part because it produces the resonance by changing the parameters either electrically or acoustically, and it detects the reflection by a stationary detector.

21 Claims, 3 Drawing Sheets

SURFACE PLASMON RESONANCE MEASURING INSTRUMENTS

TECHNICAL FIELD

This present invention relates generally to measuring instruments and specifically to instruments which utilize surface plasmon resonance (SPR) for measuring chemical or biochemical compositions but which have no moving mechanical part.

BACKGROUND OF THE INVENTION

Surface plasmon resonance is being used in biosensing, in such areas as immunoassay and nucleic acid detection Basically, surface plasmons are electromagnetic waves created along an interface between a conducting material and a non-conducting material. A common technique for their creation is to direct a beam of electromagnetic radiation into a glass prism with an angle of incidence above the critical angle so that it undergoes total internal reflection. The internal reflection creates an evanescent electromagnetic wave at a region outside of the prism adjacent to the surface. When a thin conductive film is deposited on the surface of the prism, surface plasmons will be formed.

Surface plasmon resonance occurs when the momentum (or the wave vector) and energy (i.e. frequency) of the evanescent electromagnetic wave are made to match the momentum and energy of the surface plasmons respectively. It is characterized by a sharp decrease in intensity of the reflected beam as its energy is transferred, because of the resonance, to the surface plasmons.

The wave vector $K_e$ of the evanescent wave is defined by the equation:

$$K_e = (\omega/C) \, n \sin\theta,$$

where $\omega$ is the angular frequency of the incident beam, c is the speed of light in vacuum, n is the refractive index of glass and $\theta$ is the angle of incidence- The wave vector of the surface plasmon is defined by the equation:

$$K_{sp} = (\omega/c) \, (1/\epsilon_m + 1/\epsilon_s)^{-\frac{1}{2}},$$

where $\epsilon_m$ is the real part of the dielectric constant of the metal and $\epsilon_s$ is the dielectric constant of the substance under test (or in the absence of any substance, of air) surrounding the metal.

At resonance, the wave vector of the evanescent wave is the same as that of the surface plasmons so that there is no electromagnetic wave reflected from the surface. Therefore, occurrence of the surface plasmon resonance is given by the equation:

$$K_e = K_{sp}.$$

If a periodic structure such as a grating or a surface acoustic wave is impressed upon the thin metal layer, the above equation becomes:

$$K_e + k = K_{sp}.$$

where k is the wave vector due to the periodic structure.

The above equation provides a useful tool for measuring differences between the values of $\epsilon_s$ of different materials. It also provides a useful tool for detecting the presence of trace surface chemicals in a substance that alters its $\epsilon_s$ value. By measuring the differences of $K_e$ at resonance, the changes in $\epsilon_s$ can be determined.

Surface plasmon resonance measuring instruments heretofore known which utilize the above equality condition have all measured the differences of $K_e$ by varying $\theta$ and sensing the reflected beam at different values of $\theta$, as generally shown in FIG. 1 to detect the resonance. In these prior art surface plasmon resonance measuring instruments, sensing the reflected beam at different values of $\theta$ has been accomplished by three known methods.

Under a first method, the position of the source of electromagnetic radiation is fixed. The prism is rotated in order to change the value of $\theta$. The detector for detecting the reflected beam is also rotated by $2\theta$.

Under a second method, as disclosed in "The ATR Method With Focused Light — Application to Guided Waves On A Grating" by E. Kretschmann, Vol. 26, number 1, Optics Communications, 1978, and in U.S. Pat. No. 4,997,278, entitled "Biological Sensors", issued Mar. 5, 1991 to Finlan et al, both the source and the prism are fixed. Refractive optics are then employed to spread the incident light into a cone of light beams with different values of $\theta$. The reflected beams are then detected by an array of diodes.

Under a third method, disclosed in European Patent Application Number 89304570.8, filed on May 5, 1989 by Finlan et al, the positions of both the light source and the prism are fixed. A rotating mirror is used to direct the source light to the prism at different angles of incidence. The reflection of the source beam is then deflected by another curve mirror into the detector.

All the above-described methods have relied upon moving mechanical parts to generate and/or detect the surface plasmon resonance. The disadvantages of a reliance upon moving mechanical parts are obvious — they are susceptible to fatigues, wear and tear, and they require precision tolerances that are difficult to create and maintain.

The second method suffers an additional disadvantage. Because the incident beam is spread, its intensity is reduced. In typical applications, however, the beam is additionally used to produce intensity dependent phenomenon such as fluorescence, and the effectiveness of the instrument would thus be adversely affected by the reduction of intensity resulting from this method.

The third method also suffers from other additional disadvantages. Because the beam may enter the detector from different angles, the detector needs to detect the reflected beam from different directions. Therefore, a detector having a large collection solid angle is required, and detectors having such capability are typically either expensive or less sensitive. The detector is also required to be placed at the focal point of the curved mirror, which is inconvenient and renders the overall system more susceptable to alignment errors.

Although there are other devices in the prior art that utilize surface plasmon resonance, they are not suitable for performing measurements.

What is needed is an instrument which can be used for measuring chemical compositions by measuring the dielectric constants thereof utilizing surface plasmon resonance, and one that does not have any moving mechanical part.

SUMMARY OF THE INVENTION

This invention is directed to a surface plasmon resonance (SPR) measuring instrument without any moving parts.

In one implementation, the measuring instrument comprises a block of material transparent to a beam of electromagnetic radiation. This block of material has a surface for providing internal reflection of an electromagnetic radiation beam and a metal layer on top of the surface. The instrument has a source projecting a source beam of electromagnetic radiation onto a beam steering device. The beam steering device receives the source beam and transmits it into the block at an adjustable angle of incidence to the surface. Detection of the reflected beam is performed through an array of detectors.

In a second implementation, the surface plasmon resonance (SPR) measuring instrument without any moving parts comprises means for providing internal reflection of an electromagnetic radiation beam, said means including a block of material which has a surface providing internal reflection of the electromagnetic radiation beam and a metal layer on top of the surface. A source beam of electromagnetic radiation is projected onto the surface. The means for providing internal reflection also provides a medium with an adjustable index of refraction. Surface plasmon resonance is produced by adjusting the index of refraction of the medium. An array of detectors is used to detect reflection of the source beam.

In a third implementation, the surface plasmon resonance (SPR) measuring instrument without any moving mechanical parts comprises a block transparent to a beam of electromagnetic radiation and having a surface for providing internal reflection of said electromagnetic radiation beam. A layer of periodic structure is placed on top of said surface and a layer of conductive material is placed on top of said layer of periodic structure. A source providing a source beam of electromagnetic radiation to said surface of said block to produce internal reflection. The periodic structure is used to produce the surface plasmon resonance by adjusting the value of K. A detector of electromagnetic radiation is coupled to said block for detecting reflection of said source beam from said surface.

DESCRIPTION OF THE PREFERRED EMBODIMENT

A. SPR by deflecting the electromagnetic radiation

Figure 1:
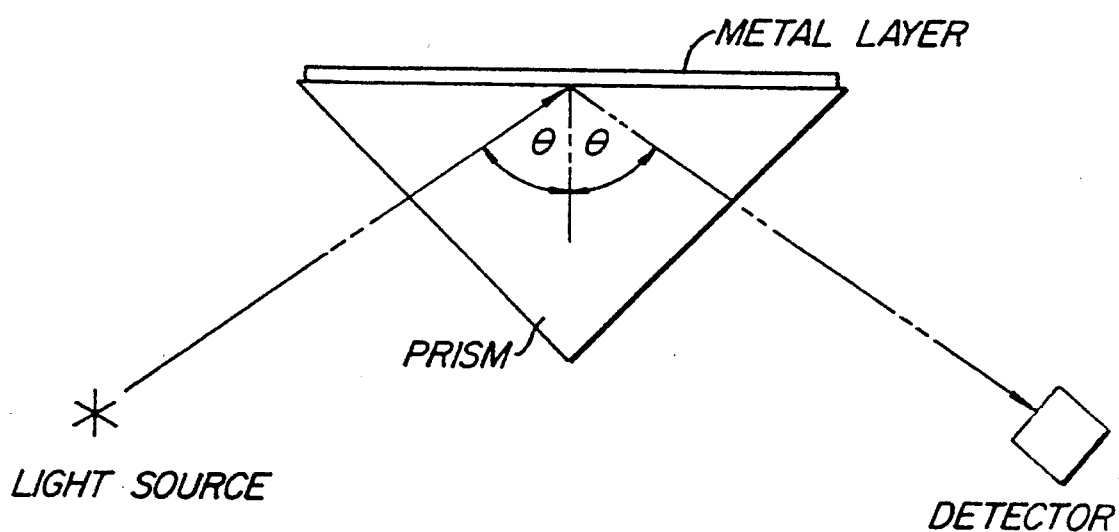
FIG. 1 illustrates generally how surface plasmon resonance is generated.
Figure 2:
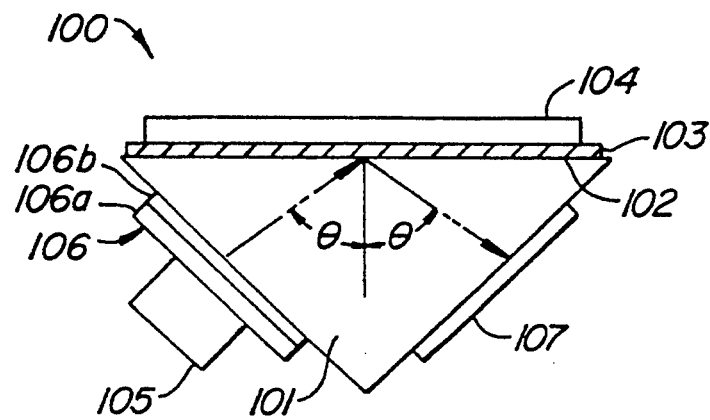
FIG. 2 illustrates a SPR measuring instrument utilizing beam deflection.

FIG. 2 illustrates a SPR measuring instrument 100 which has no moving mechanical part. The instrument 100 comprises a block of transparent material (transparent to electromagnetic waves) 101 such as a glass prism. The block 101 has a surface 102 for providing internal reflection of a beam of electromagnetic radiation when such beam is projected to the surface 102 at appropriate angles of incidence.

On top of the surface 102 of the transparent block 101 is a metal layer 103 of thickness preferably close to 50 nm. On top of the metal layer 103 is the test sample 104.

A beam of electromagnetic radiation is provided from a source 105 such as a diode laser. The beam of electromagnetic radiation from the source 105 passes through a beam steering device 106 before it enters the block 101.

When the beam of electromagnetic radiation incident onto the surface 102 at an angle of incidence above the critical angle, it undergoes an internal reflection and produces surface plasmons along the interface between the metal layer 103 and the test sample 104.

The angle of incidence of the beam at the surface 102 is adjustable by adjusting the beam deflection device 106.

In a first implementation, the beam deflection device 106 comprises a layer of electro-optic material, such as quartz of several centimeters thick. The angle of incidence of the source at the surface 102 can be adjusted by applying an electrical signal at a voltage of one to two kilovolt to the device 106 and varying the voltage of the signal. The angle of incidence of the beam at surface 102 can then be determined as a function of the voltage applied. (See "Introduction to Optical Electronics", A. Yariv, published by Holt, Rhinehart and Winston, New York 1976, page 267). In order for the beam to be projected to the same point on the surface 102 even at different angles of incidence, an additional layer of electro-optic cells can be used. In effect, the layer 106 would comprise one layer 106a connected to one electrical source (not shown) and another layer 106b connected to another electrical source (not shown). The point of incidence as well as the angle of incidence can both be adjusted by varying the voltages applied by the two independent electrical sources.

In another implementation, the beam deflection device 106 comprises a layer of acousto-optic material of several centimeters thick. Beam deflection under this method is known in the art (see A. Yariv, supra, pages 349–351). The angle of incidence of the beam at surface 102 can be adjusted by applying an electrical signal with a frequency of 50 to 200 megahertz to the acousto-optic material and varying the frequency of the signal. The angle of incidence of the beam at surface 102 can then be determined as a function of the frequency. In order for the beam to be projected to the same point on the surface 102 even at different angles of incidence, an additional layer of acousto-optic cells can be used. In effect, the layer 106 would comprise one layer 106a connected to one electrical source (not shown) and another layer 106b connected to another electrical source (not shown). The point of incidence as well as the angle of incidence can both be adjusted by varying the frequencies of the electrical signals applied by the two independent electrical sources.

The reflected beam is received by an array of detectors, such as an array of diodes 107. Each of the diodes in the array 107, upon receiving the reflected beam, generates a current that is proportional to the intensity of the reflected beam. The intensity of the reflected beam can then be measured as a function of the current generated.

By altering the angles of incidence, and continually sensing the current from the array of diodes 107, the resonance can be detected.

B. Producing SPR by changing index of refraction

Figure 3:
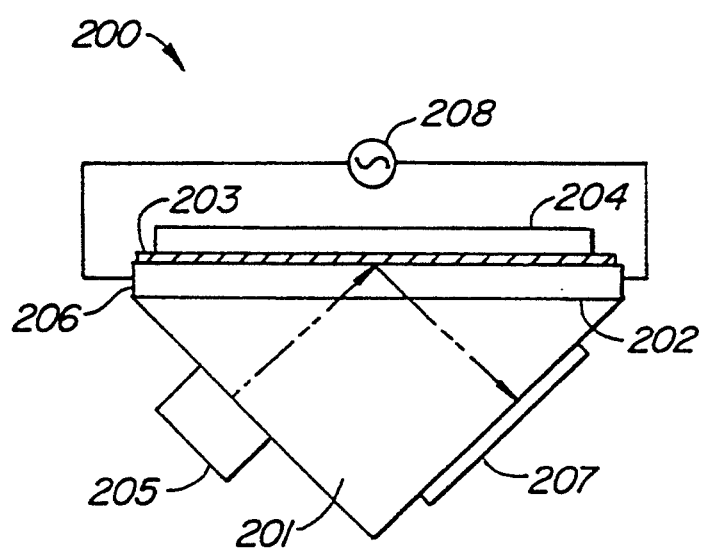
FIG. 3 illustrates a SPR measuring instrument that utilizes a material having an adjustable index of refraction.

FIG. 3 illustrates another surface plasmon resonance measuring instrument 200 which has no moving mechanical part.

The instrument 200 comprises a transparent block 201, such as a glass prism. On top of a surface 202 of the block 201 is a layer 206 of material having an adjustable index of refraction. On top of the layer 206 is a metal layer 203. On top of the metal layer 203 is the test sample 204. The interface between the metal layer 203 and the test sample 204 provides the metaldielectric interface for producing the surface plasmons when a beam of electromagnetic radiation is projected onto the surface 202 at an appropriate angle of incidence. That beam of electromagnetic radiation is provided from a source 205.

Layer 206 is in general made up of material whose index of refraction can be varied. An example of such material is a crystalline material such as quartz. Preferably, however, the quartz is cut at an angle that does not affect the polarization of the source light.

Liquid crystal films can advantageously be used to form layer 206, as the refractive index of some liquid crystals can be changed by a value as high as 0.05.

An adjustable electrical signal is applied to by source 208 to the layer 206. The refractive index of the material in layer 206 would change as a function of the amplitude of the signal. By adjusting the signal 208 the condition for producing the resonance can be maintained. (See A. Yariv, supra)

Other materials can be used to form layer 206. As an example, a multiple quantum well structure, as disclosed by T.Y. Hsu, et al. in "Amplitude and phase modulation in a 4 um-thick GaAs/AlGaAs Multiple Quantum Well Modulator", Elect. Lett, 24, 603 (1988) can be used. The disclosed well structure is capable of providing a change of 0.04 at an applied voltage of approximate 10 volt.

Semiconductor materials can also be used to form layer 206, as their refractive indices change as a function of the density of charge carriers, which may be altered by an applied voltage or by irradiation with light whose energy is greater than the bandgap.

$BaTiO_3$ whose refractive index changes when exposed to light, as disclosed by Y.R. Shen, in "The Principles of Laser Optics", Wiley, New York, 1984, can also be used. The refractive index changes as a function of the intensity of the light applied.

To detect the resonance, an array of detectors 207, such as an array of diodes, are used to sense the intensity of reflected beam.

C. Producing SPR by periodic material

Figure 4:
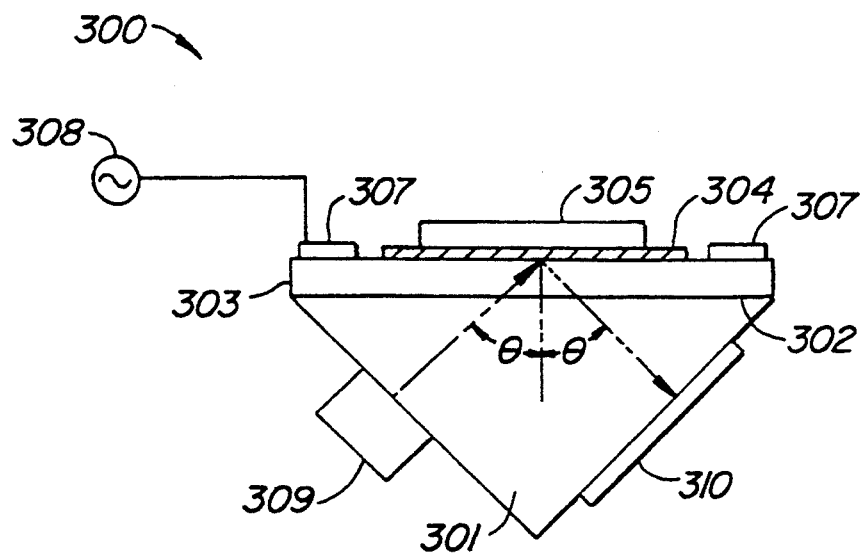
FIG. 4 illustrates a SPR measuring instrument utilizing a periodic structure.

FIG. 4 illustrates yet another surface plasmon resonance measuring instrument 300 that has no moving mechanical part.

The instrument 300 comprises a transparent block 301, such as a glass prism. On top of a surface 302 is a substrate 303. Preferably a refractive index matching fluid is placed in between the surface 302 of the block and the substrate 303. On top of the substrate 303 is a metal layer 304. On top of the metal layer 304 is the test sample 305. The interface between the metal layer 304 and the test sample 305 provides the metal-dielectric interface for producing the surface plasmons, when a beam of electromagnetic radiation is projected onto the surface 302 at an appropriate angle of incidence. That beam is provided from a source 309.

On top of the substrate 303 is a plurality of interdigital transducers 307. A signal generator 308 is connected to the interdigital transducers 307. The signal generator 308 generates sinusoidal signals that, through the interdigital transducer 307, produce a surface acoustic wave in the substrate 303.

The substrate 303 is made of material such as $LiNbO_3$. By using $LiNbO_3$, a center frequency greater than 3.5 GHz can be generated in the substrate 303. The spacing between individual interdigital transducer 307 is preferably non-uniform, thereby making the frequency of the surface acoustic wave in the substrate 303 tunable by at least 10% to 20%.

Surface acoustic waves can also be generated by an interference of two light beams, such as laser beams, on a semiconductor surface. The relaxation of electrons and holes created by the interference causes local heating and surface acoustic waves with a wavelength determined by the periodicity of the interference. Surface plasmon resonance can therefore be produced by tuning the wave vector K which in turn can be tuned by steering or changing the wavelength of the two laser beams.

E. Other methods of producing SPR

Figure 5:
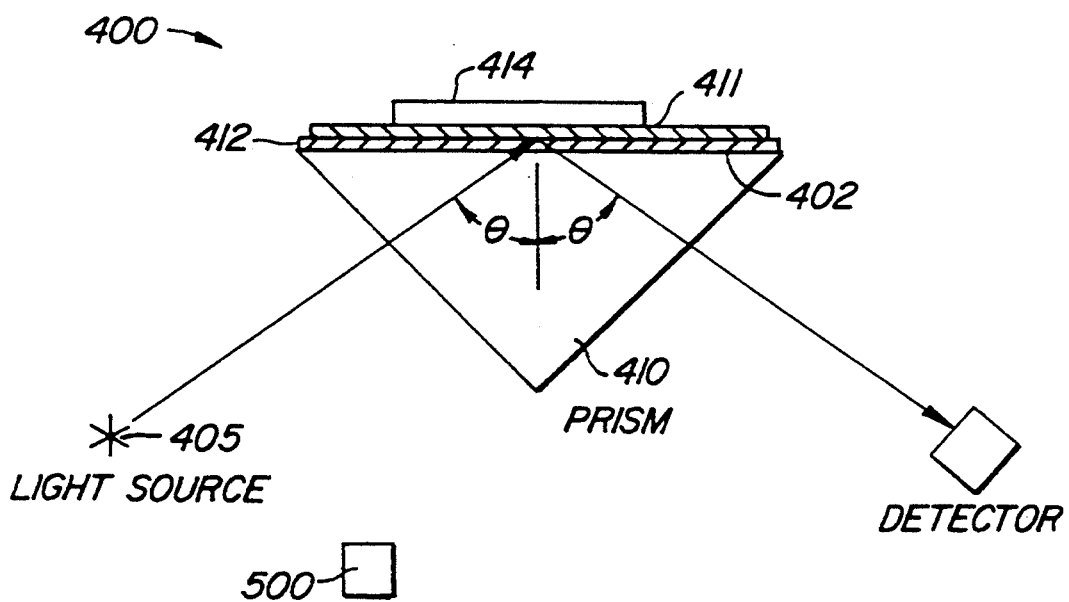
FIG. 5 illustrates a SPR measuring instrument in another embodiment of the invention.

A SPR measuring instrument without any moving mechanical parts can also be built using the configuration 400 illustrated in FIG. 5. However, the prism 410 would be made of a dispersive material. The wave vector of the light would depend on the frequency of the light incident on surface 402. Alternatively, prism 410 is made from a non-dispersive material, but a layer of dispersive material 412 can be deposited between the prism surface and the metal layer 411, adapted to contact a test sample 414. Surface plasmons are generated by projecting a beam of electromagnetic radiation into the prism at appropriate angles of incidence. In either case, namely where prism 410 is dispersive without layer 412, and where prism 410 is not dispersive but dispersive layer 412 is employed, resonance of the surface plasmons is attained by tuning the frequency of the electromagnetic radiation from tunable source 405. Widely tunable solid-state electromagnetic radiation sources are currently available.

Still another SPR measuring instrument without any moving mechanical part can be built by changing the temperature of either the metal layer 411 or the prism 410 of the instrument 400 generally shown in FIG. 5. The temperature change changes the refractive index of the prism 10 or the dielectric constant of the metal layer 11. The temperature change can be caused locally by passing a current from a current source (not shown) through the metal layer, without significantly affecting the temperature of the prism. The temperature can also be changed by a radiation source such as source 500 that can be used to heat the prism and metal layer. Obviously, cooling means may be used instead to cool the prism or metal layer or both if desired.

Although this invention is described with reference to specific parameters and implementations, it will be understood that various modifications can be made thereto without substantive departure from the scope of the invention, which is defined by the following claims.

We claim:

1. A surface plasmon resonance (SPR) instrument, comprising:
   a block of material transparent to an electromagnetic beam, the block of material having a first surface;
   a crystalline material having an amplitude that is electrically modulated, the amplitude corresponding to an adjustable index of refraction, having a second surface for providing internal reflection of the electromagnetic beam;
   a source of electricity supplying electricity with adjustable amplitude to modulate the adjustable index of refraction of said crystalline material; a conductive layer adjacent to the second surface, the conductive layer adapted to contact a sample;
   an electromagnetic beam radiating to the second surface to produce internal reflection; and
   a detector of electromagnetic radiation coupled to the block for detecting reflection of the source beam from the second surface.

2. A SPR instrument as in claim 1, wherein said crystalline material is quartz.

3. A surface plasmon resonance (SPR) instrument, comprising:
   a block of material transparent to an electromagnetic beam, the block of material having a first surface;
   a liquid crystal material having an amplitude that is electrically modulated, the amplitude corresponding to an adjustable index of refraction, having a second surface for providing internal reflection of the electromagnetic beam;
   a source of electricity supplying electricity with adjustable amplitude to modulate the adjustable index of refraction of said liquid crystal material;
   a conductive layer adjacent to the second surface, the conductive layer adapted to contact a sample;
   an electromagnetic beam radiating to the second surface to produce internal reflection; and
   a detector of electromagnetic radiation coupled to the block for detecting reflection of the source beam from the second surface.

4. A surface plasmon resonance (SPR) instrument comprising:
   a block of material transparent to an electromagnetic beam, the block of material having a first surface;
   a semiconductor material having an amplitude that is electrically modulated, the amplitude corresponding to an adjustable index of refraction, having a second surface for providing internal reflection of the electromagnetic beam;
   a source of electricity supplying electricity with adjustable amplitude to modulate the adjustable index of refraction of said semiconductor material;
   a conductive layer adjacent to the second surface, the conductive layer adapted to contact a sample;
   an electromagnetic beam radiating to the second surface to produce internal reflection; and
   a detector of electromagnetic radiation coupled to the block for detecting reflection of the source beam from the second surface.

5. A surface plasmon resonance (SPR) instrument, comprising:
   a block of material transparent to an electromagnetic beam, the block of material having a first surface;
   a multiple quantum well structure having an amplitude that is electrically modulated, the amplitude corresponding to an adjustable index of refraction, having a second surface for providing internal reflection of the electromagnetic beam;
   a source of electricity supplying electricity with adjustable amplitude to modulate the adjustable index of refraction of said structure;
   a conductive layer adjacent to the second surface, the conductive layer adapted to contact a sample;
   an electromagnetic beam radiating to the second surface to produce internal reflection; and
   a detector of electromagnetic radiation coupled to the block for detecting reflection of the source beam from the second surface.

6. A surface plasmon resonance (SPR) instrument, comprising:
   a block of material transparent to an electromagnetic beam, the block of material having a first surface;
   a photo refractive material having an amplitude that is electrically modulated, the amplitude corresponding to an adjustable index of refraction, having a second surface for providing internal reflection of the electromagnetic beam;
   a light source supplying light with adjustable intensity to modulate the adjustable index of refraction of said photo refractive material;
   a conductive layer adjacent to the second surface, the conductive layer adapted to contact a sample;
   an electromagnetic beam radiating to the second surface to produce internal reflection; and
   a detector of electromagnetic radiation coupled to the block for detecting reflection of the source beam from the second surface.

7. A SPR instrument as in claim 6, wherein said photo refractive material comprises a layer of $BaTiO_3$.

8. A surface plasmon resonance (SPR) instrument without any moving mechanical parts, comprising:
   a block of material transparent to a source beam of electromagnetic radiation, said block of material having a first surface,
   means for providing a periodic structure adjacent to said first surface, wherein said means for providing periodic structure comprises a layer of material for generating surface acoustic waves (SAW), and a plurality of non-uniformly spaced interdigital transducers in contact with said material, said instrument further comprising a source of electricity providing electrical signals to said interdigital transducers, wherein said periodic structure providing means further comprises a second surface for providing internal reflection of said source beam,
   a layer of conductive material adjacent to said second surface, said layer of conductive material adapted to contact a sample, and
   a detector of electromagnetic radiation coupled to said block for detecting reflection of said source beam from said second surface.

9. A SPR instrument as in claim 8, wherein said material for generating SAW is $LiNbO_3$.

10. A SPR instrument as in claim 9, wherein said source of electricity provides electrical signals at 3.5 GHz.

11. A SPR instrument as in claim 8, wherein said means for providing a periodic structure comprises a layer of semiconductor material and a first and a second light source generating light beams with adjustable wavelengths and producing an interference in said semiconductor material.

12. A SPR instrument as in claim 11, wherein said light sources are laser sources.

13. A surface plasmon resonance (SPR) instrument without any moving mechanical part, comprising:
- a block of non-dispersive material transparent to a tunable source beam of electromagnetic radiation and having a first surface,
- a layer of dispersive material adjacent to said surface, said layer of dispersive material having a second surface for providing internal reflection of said tunable source beam of electromagnetic radiation,
- a layer of conductive material adjacent to said second surface, said layer of conductive material adapted to contact a sample, and
- a detector of electromagnetic radiation coupled to said block for detecting reflection of said source beam from said second surface.

14. A surface plasmon resonance (SPR) instrument without any moving mechanical part, comprising:
- a block material transparent to a source beam of electromagnetic radiation and having a surface for providing internal reflection of said source beam of electromagnetic radiation,
- a layer of conductive material adjacent to said surface, said layer adapted to contact a sample, and
- a detector of electromagnetic radiation coupled to block for detecting reflection of said source beam from said surface, and
- means for adjusting temperature of said block of material to change its refractive index.

15. The instrument of claim 14, wherein said temperature adjusting means comprises means for applying radiation to the block and the layer of conductive material.

16. A surface plasmon resonance (SPR) instrument without any moving mechanical part, comprising:
- a block material transparent to a source beam of electromagnetic radiation and having a surface for providing internal reflection of said source beam of electromagnetic radiation,
- a layer of conductive material adjacent to said surface, said layer adapted to contact a test sample, and
- a detector of electromagnetic radiation coupled to said block for detecting reflection of said source beam from said surface, and
- means for adjusting temperature of said layer of conductive material to change its dielectric constant.

17. The instrument of claim 16, wherein said temperature adjusting means comprises means for applying a current to said layer of conductive material.

18. A method for detecting surface plasmon resonance associated with a test sample which is placed adjacent to a surface plasmon resonance instrument, said method being performed without the use of any moving mechanical part, said method comprising the steps of:
- (a) transmitting a source beam of electromagnetic radiation into a block of material transparent to said source beam of electromagnetic radiation, said block of material including a layer of transparent material within said block, said layer of transparent material having an adjustable index of refraction and having a surface for providing internal reflection of said source beam;
- (b) repeatedly altering the index of refraction of said layer of transparent material by applying an adjustable electrical signal to said layer of transparent material;
- (c) repeatedly detecting a reflection of said source beam and a corresponding amplitude thereof, and
- (d) detecting surface plasmon resonance associated with a test sample based upon relative amplitudes of said detected reflection of said source beam.

19. A method for detecting surface plasmon resonance associated with a test sample which is placed adjacent to a surface plasmon resonance instrument, said method being performed without the use of any moving mechanical part, said method comprising the steps of:
- (a) transmitting a source beam of electromagnetic radiation into a block of material transparent to said source beam, said block of material including a layer of substrate suitable for generating surface acoustic waves therein, said layer of substrate having a surface for providing internal reflection of said source beam;
- (b) generating surface acoustic waves in said layer of substrate, said surface acoustic waves being adjustable in frequency;
- (c) repeatedly varying the frequency of said surface acoustic waves;
- (d) repeatedly detecting a reflection of said source beam and a corresponding amplitude thereof, and
- (e) detecting surface plasmon resonance associated with a test sample based upon relative amplitudes of said detected reflection of said source beam.

20. A method for detecting surface plasmon resonance associated with a test sample which is placed adjacent to a surface plasmon resonance instrument, said method being performed without the use of any moving mechanical part, said method comprising the steps of:
- (a) transmitting a source beam of electromagnetic radiation into a block of material transparent to said source beam, said block having a surface for providing internal reflection of said source beam;
- (b) repeatedly adjusting the temperature of said block of material to change its refractive index;
- (c) repeatedly detecting a reflection of said source beam and a corresponding amplitude thereto, and
- (d) detecting surface plasmon resonance associated with a test sample based upon relative amplitudes of said detected reflection of said source beam.

21. A method for detecting surface plasmon resonance associated with a test sample which is placed adjacent to a surface plasmon resonance instrument, said method being performed without the use of any moving mechanical part, said method comprising the steps of:
- (a) transmitting a source beam of electromagnetic radiation into a block of material transparent to said source beam of electromagnetic radiation, said block having a surface for providing internal reflection of said source beam;
- (b) repeatedly adjusting the temperature of said layer to change its dielectric constant;
- (c) repeatedly detecting a reflection of said source beam and a corresponding amplitude thereof, and
- (d) detecting surface plasmon resonance associated with a test sample based upon relative amplitudes of said detected reflection of said source beam.

* * * * *